United States Patent
Qian et al.

(10) Patent No.: US 8,575,554 B2
(45) Date of Patent: Nov. 5, 2013

(54) METHODS AND SYSTEMS FOR SCATTER ESTIMATION IN POSITRON EMISSION TOMOGRAPHY

(75) Inventors: Hua Qian, Clifton Park, NY (US); Ravindra Mohan Manjeshwar, Glenville, NY (US); Kris Filip Johan Jules Thielemans, London (GB)

(73) Assignee: General Electric Company, Niskayuna, NY (US)

( * ) Notice: Subject to any disclaimer, the term of this patent is extended or adjusted under 35 U.S.C. 154(b) by 102 days.

(21) Appl. No.: 13/191,205

(22) Filed: Jul. 26, 2011

(65) Prior Publication Data

US 2013/0026370 A1  Jan. 31, 2013

(51) Int. Cl.
*G01T 1/164* (2006.01)
*A61B 6/00* (2006.01)
*G06K 9/00* (2006.01)

(52) U.S. Cl.
USPC ........................ 250/363.03; 600/436; 382/131

(58) Field of Classification Search
USPC ........................ 250/363.03; 600/436; 382/131
See application file for complete search history.

(56) References Cited

U.S. PATENT DOCUMENTS

| | | | |
|---|---|---|---|
| 6,590,213 B2 | 7/2003 | Wollenweber | |
| 6,631,284 B2 | 10/2003 | Nutt et al. | |
| 7,129,496 B2 | 10/2006 | Stearns et al. | |
| 7,312,455 B2 | 12/2007 | Manjeshwar et al. | |
| 7,381,959 B2 | 6/2008 | Manjeshwar et al. | |
| 7,397,035 B2 | 7/2008 | Watson | |
| 7,603,165 B2 | 10/2009 | Townsend et al. | |
| 7,714,291 B2 | 5/2010 | Thielemans et al. | |
| 2006/0151705 A1* | 7/2006 | Manjeshwar et al. | ... 250/363.03 |
| 2006/0178575 A1* | 8/2006 | Piacsek et al. | ............... 600/413 |
| 2007/0085013 A1* | 4/2007 | Watson | ................... 250/363.07 |
| 2010/0078568 A1 | 4/2010 | Byars et al. | |

OTHER PUBLICATIONS

S D Wollenweber, Parameterization of a Model-Based 3-D PET Scatter Correction, Jun. 2002, IEEE Transactions of Nuclear Science, vol. 49, pp. 722-727.*
S.D. Wollenweber, Parametization of a Model-Based 3-D PET Scatter Correction, Jun. 2002, IEEE Transactions on Nuclear Science, vol. 49, No. 3, pp. 722-727.*
Hua Qian, Ravi Manjeshwar, & Kris Thielemans, A Comparative Study of Multiple Scatter Estimations in 3D PET, Nov. 2010, Nuclear Science Symposium Conference Record (NSS/MIC), Knoxville, TN, pp. 2700-2702.*
IP.com Anonymous Disclosure, Adaptive Multiple-Scatter Estimation Method for Model-Based Scatter Correction in Positron Emission Tomography, IP.com No. IPCOM000117352D, Mar. 31, 2005, IP.com Prior Art Database Technical Disclosure, pp. 1-6.*
Andrew S. Goggin and John M. Olfinger, a Model for Multiple Scatters in Fully 3D PET, Proc IEEE Nucl. Sci. Symp. Med. Imaging Conf., vol. 4, pp. 1609-1613, 1995.

(Continued)

*Primary Examiner* — David Porta
*Assistant Examiner* — Jeremy S Valentiner
(74) *Attorney, Agent, or Firm* — Jenifer Haeckl (57) ABSTRACT

Methods and systems for multiple scatter estimation in Positron Emission Tomography (PET) are provided. One method includes determining attenuation sinograms and determining a varying convolution kernel as a function of the attenuation sinograms, wherein the kernel varies in amplitude and width over a radial length of a PET imaging system. The method also includes using the varying convolution kernel to estimate multiple PET scatter.

20 Claims, 7 Drawing Sheets

(56) References Cited

OTHER PUBLICATIONS

M. Bergstrom, et al., Correction for Scattered Radiadon in a Ring Detector Positron Camera by Integral Transformation of the Projections, Journal of Computer Assisted Tomography, 7(1):42-50, Feb. 1983, Raven Press, NY.

John M. Ollinger and Gerald C. Johns, Model-Based Scatter Correction for Fully 3D PET, Washington University, St. Louis, MO, Supported by Grant No. CA54959 from the National Cancer Institute, 1994 IEEE. pp. 1264-1268.

* cited by examiner

METHODS AND SYSTEMS FOR SCATTER ESTIMATION IN POSITRON EMISSION TOMOGRAPHY

BACKGROUND

The subject matter disclosed herein relates generally to diagnostic imaging systems, and more particularly to Positron Emission Tomography (PET) imaging systems and scatter correction for PET imaging systems.

PET imaging systems typically generate images depicting the distribution of positron-emitting nuclides in patients based on coincidence emission events detected using a detector system, usually configured as a ring assembly of detector blocks. The positron interacts with an electron in the body of the patient by annihilation, and then the electron-positron pair is converted into two photons. The photons are emitted in opposite directions along a line of response. The annihilation photons are detected by detectors on both sides of the line of response of the detector ring. The image is then generated based on the acquired emission data that includes the annihilation photon detection information.

Coincidence detection circuits connected to the detectors record only photons that are detected within a narrow time window by detectors located on opposite sides of a line joining the detectors to the point of annihilation. These detections are deemed to have occurred "simultaneously" and are termed coincidence events. The coincidence events indicate that the positron annihilations occurred along a line joining the two opposing detectors. The coincidence events detected by the PET detector ring assembly are typically stored within data structures called emission sinograms. An emission sinogram is a histogram of the detected coincidence events where each of a plurality of bins in the histogram represents a potential detector pair element.

Some gamma rays are deflected from an original direction due to interaction with a body part before reaching the detectors. Such events are termed scatter events. These scatter events, if used during image reconstruction, result in biased estimates of the activity distribution in the patient. Thus, a true activity distribution of radio-activity in the scanned body part of the patient does not result.

In order to correct for scattered coincidences in PET scanners, various scatter correction methods are known. Scatter corrections are generally performed in two steps, which are a single scatter correction step and a multiple scatter correction step. Model-based single scatter simulation methods are often used for the single scatter correction. For correction of multiple scatters, model-based simulation methods can be used, but are computationally intensive. Additionally, convolution methods may be used with a simple fixed kernel. However, these convolution methods can reduce the accuracy of the scatter estimation.

BRIEF DESCRIPTION

In accordance with various embodiments, a non-transitory computer readable storage medium for estimating multiple scatter in Positron Emission Tomography (PET) imaging using a processor is provided. The non-transitory computer readable storage medium includes instructions to command the processor to determine attenuation sinograms and determine a varying convolution kernel as a function of the attenuation sinograms, wherein the kernel varies in amplitude and width over a radial length of a PET imaging system. The non-transitory computer readable storage medium also includes instructions to command the processor to use the varying convolution kernel to estimate multiple PET scatter.

In accordance with other embodiments, a method for estimating multiple scatter in Positron Emission Tomography (PET) imaging is provided. The method includes determining attenuation sinograms and determining a varying convolution kernel as a function of the attenuation sinograms, wherein the kernel varies in amplitude and width over a radial length of a PET imaging system. The method also includes using the varying convolution kernel to estimate multiple PET scatter.

In accordance with yet other embodiments, a Positron Emission Tomography (PET) imaging system is provided that includes a gantry and a detector ring mounted to the gantry, wherein the detector ring has a plurality of detector elements. The PET imaging system also includes a scatter estimation module configured to (i) determine attenuation sinograms, (ii) determine a varying convolution kernel as a function of the attenuation sinograms, wherein the kernel varies in amplitude and width over a radial length of the gantry, and (iii) use the varying convolution kernel to estimate multiple PET scatter.

DETAILED DESCRIPTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide a scatter estimation method for Positron Emission Tomography (PET) systems. In particular, a convolution method for multiple scatter estimation in three-dimensional (3D) PET is described herein. The method in some embodiments includes using a kernel that has an amplitude and width that varies as a function of a filtered attenuation sinogram that is obtained from a Computed Tomography (CT) scan. The method may also include filtering the attenuation sinograms and optimizing the parameters using, for example, Monte Carlo simulation data. By practicing at least some embodiments, one technical effect includes allowing scatter estimation for a larger range of imaged objects (e.g., different sized patients). At least one other technical effect of at least some embodiments is improved image quality of the PET scan, such as with respect to image uniformity and quantification.

It should be noted that as used herein, a kernel is generally a set of elements used for mapping. For example, a convolution kernel may be a kernel that maps from one scatter distribution to another scatter distribution, such as from a single scatter distribution (e.g., an emitted photon that is scattered or is deflected once) to a multiple scatter distribution (e.g., an emitted photon that scatters or is deflected multiple times).

Figure 1:
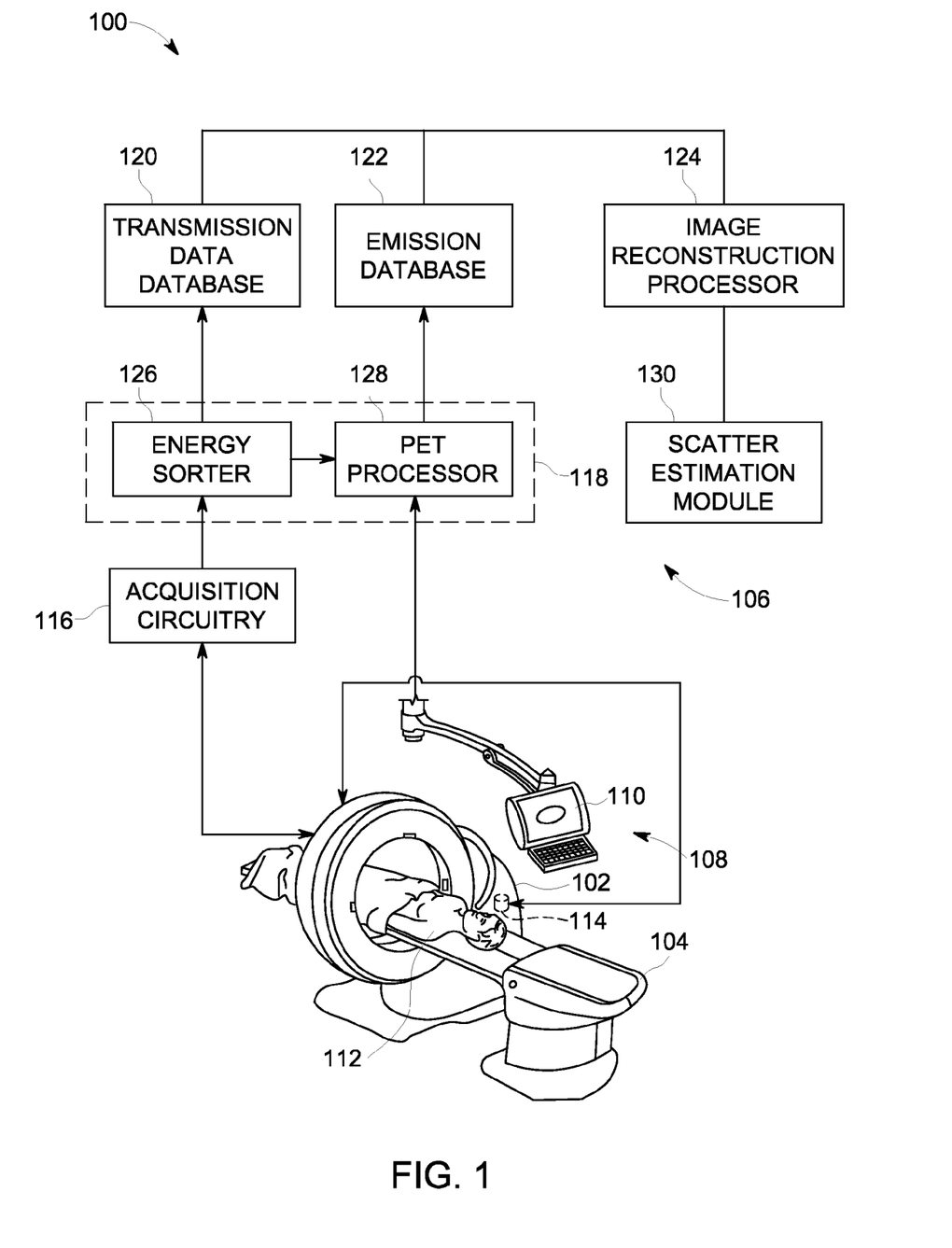
FIG. 1 is a schematic block diagram illustrating a Positron Emission Tomography/Computed Tomography (PET/CT) dual imaging system formed in accordance with various embodiments.

The various embodiments may be implemented, for example, in a medical imaging system 100 illustrated in FIG. 1, which is shown as a PET system that includes Computed Tomography (CT) imaging capabilities, for example, configured as a multi-modality imaging system, such as a PET/CT imaging system. However, it should be appreciated that although the various embodiments are described in connection with a PET/CT imaging system having a particular configuration, the various embodiments may be implemented in connection with PET/CT imaging systems have different configurations and components, as well as with other types of dual-modality imaging systems, for example, a Single Photon Emission Computed Tomography (SPECT)/CT imaging system or a PET/Magnetic Resonance (PET/MR) imaging system. Other modalities may be used, for example, an ultrasound system, Magnetic Resonance Imaging (MRI) or any other system capable of generating physiological activity distribution images and/or tomographic images. Moreover, the imaging detectors may be of different types and configurations. Also, although the various embodiments are described in connection with a multi-modality imaging system, the various embodiments may be implemented in a one or more single modality imaging systems.

Thus, in one embodiment, the medical imaging system 100 is a PET/CT imaging system as illustrated in FIG. 1. It should be noted that in some embodiments, the CT data is acquired prior to obtaining the PET data. However, the data may be acquired in different orders and combinations thereof (e.g., in an interleaved manner).

The medical imaging system 100 generally includes a gantry 102, a patient table 104, and a processing and control system 106 including a user input 108 with a display 110. The gantry 102 provides mechanical support for imaging devices such as, for example, detectors, scanners and transmitters that are used for scanning a patient or other object (e.g., a phantom). The gantry 102 houses imaging devices such as, for example, PET detectors or x-ray detectors. It should be noted that the PET portion of the system in one embodiment is a stationary annular detector, namely a ring of detectors.

The imaging devices on the gantry 102 acquire image data by scanning a patient or other object on the patient table 104. Moving the patient table 104 enables the scanning of various portions of the patient or object. The patient table 104 lies along the axis of gantry 102, which is known as a viewing area along an examination axis and can be moved along this axis. The patient table 104 can be positioned at various axial positions along the axis. In some embodiments, the gantry 102 includes a plurality of PET detectors that are fixed and spaced on gantry 102, which are positioned radially outward from the axis and that may be configured as one or more rings of detectors. In accordance with other embodiments, the gantry 102 includes a plurality of detectors that are rotatable about the axis. For CT imaging, such as to acquire attenuation information, a rotating detector and a source, for example, an x-ray tube 114 may be provided and optionally a stationary detector ring for CT imaging may be provided. In other embodiments, a separate imaging gantry is provided for CT imaging.

The processing and control system 106 controls the positioning of the patient table 104, as well as receiving data acquired during scanning. In various embodiments, the processing and control system 106 controls the medical imaging system 100 to acquire, for example, image information and/or attenuation information of a volume of interest, for example, a patient and as described in more detail herein. For example, annihilation events may be detected as emission data (e.g., emitted from a patient injected with a radionuclide) as well as transmission data from signals transmitted by a transmission source, such as the x-ray tube 114, which pass through the volume of interest. The transmission signals are attenuated when the signals pass through the volume of interest and the detectors collect data that is attenuated after the transmission signals pass through the volume of interest.

Various processors, sorters, and databases are used to acquire and manipulate emission and transmission data, which is used in accordance with various embodiments. The processors, sorters and databases of FIG. 1 include acquisition circuitry 116, an acquisition processor 118, a transmission data database 120, an emission database 122, and an image reconstruction processor 124. The acquisition processor 118 is programmed to acquire emission data, for example, in a list mode and/or a sinogram mode, as described in more detail below, and generate an image based on the emission data acquired in the list mode and/or the emission data acquired in the sinogram mode, which is scatter corrected. The medical imaging system 100 may also include other computing components.

In some embodiments, an energy sorter 126 provides, for example, time, location, and energy data to a PET processor 128. The PET processor 128 generally uses the received data to identify pairs of data, also known as coincidence pairs, coincident pair lines and lines of response, corresponding to annihilation events that occurred inside the region of interest. After the acquisition processor 118 identifies an annihilation event, the acquisition processor 118 updates data in the emission data database 122 to store information relating to the annihilation events. X-ray CT data is also stored in the transmission data database 120 based on transmission signals that pass through the volume of interest (e.g., phantom) and are detected.

Thus, after an acquisition session has been completed and sets of transmission and emission data have been stored in databases 120 and 122, respectively, the image reconstruction processor 124 accesses the data in the databases 120 and 122 and uses the accessed data to generate images that may be requested by a system operator. Additionally, the sets of transmission and emission data are used by a scatter estimation module 130 to perform scatter estimation, particularly multiple scatter estimation (e.g., estimating multiple 3D PET scatter) as described in more detail herein.

It should be noted that the reconstruction of the emission data may be performed in any suitable manner using any type of image reconstruction process, such as analytical image reconstruction algorithms known in the art. In one embodiment, the images are reconstructed from the scan of the patient or object correcting for multiple scatters using a convolution method having a kernel with an amplitude and width that varies as a function of a filtered attenuation sinogram that is obtained from the CT scan.

Figure 2:
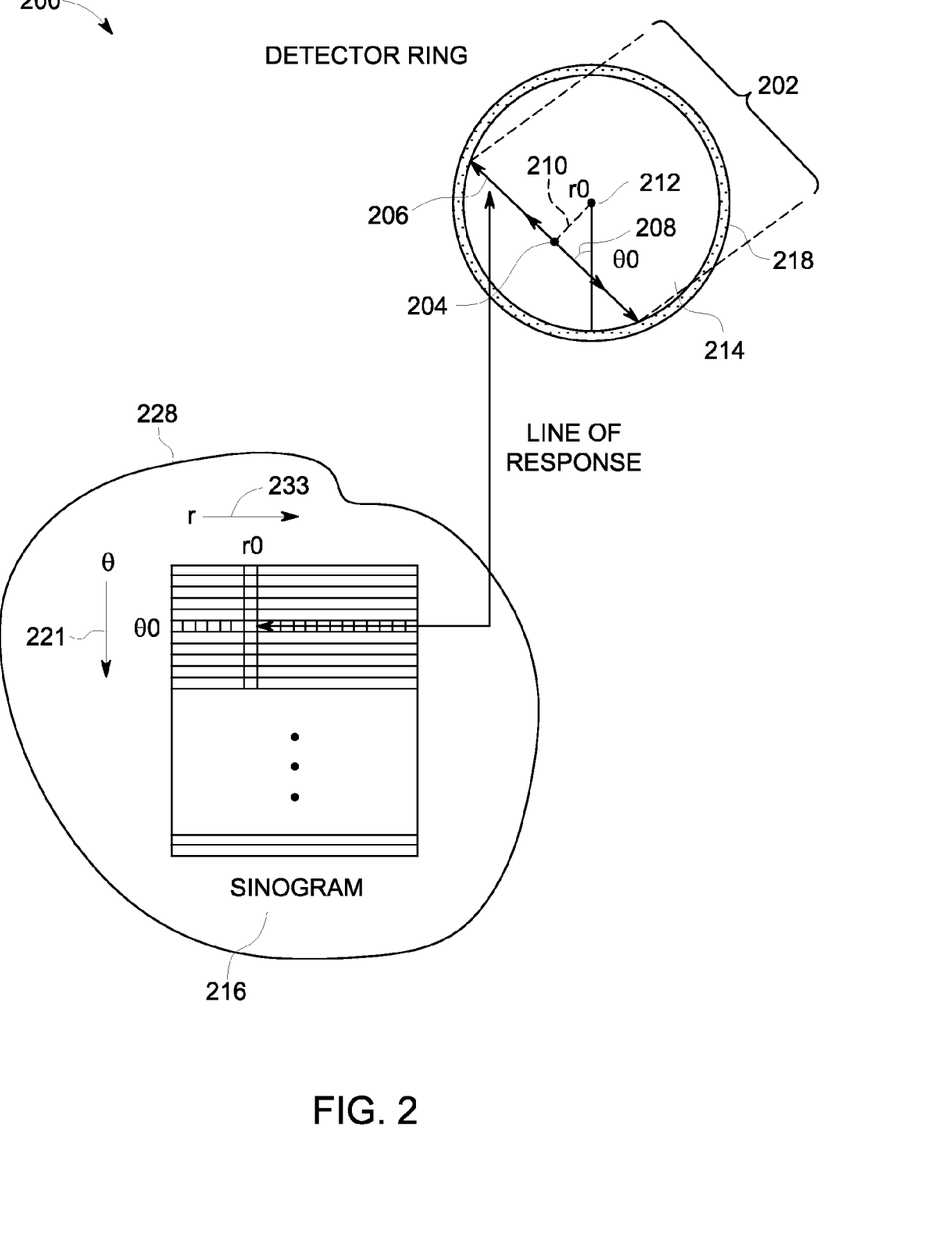
FIG. 2 is a diagram of a PET detector ring and an illustration of the construction of a PET sinogram used in various embodiments.

For example, as shown in FIG. 2, illustrating a sinogram construction process 200, the energy sorter 126 (shown in FIG. 1) receives a coincidence event pair 202 of an annihilation event 204 and identifies a corresponding line of response 206. Each line of response 206 may be identified by an angle ($\theta$) 208 and a distance (r) 210 from a center 212 of the field of view 214. The array of the responses 206 is known as a sinogram 216, which may be stored as a 2D or 3D distribution. The sinogram 216, which is an emission sinogram, is essentially a histogram of detected coincidence events where each of a plurality of bins in the histogram represents a potential detector pair element.

It should be noted that the imaging system 100 may include multiple rings 218 of detectors covering, for example, 15-25 centimeters in the axial direction. The detectors typically include radiation detectors with sufficiently high timing resolution. The high timing resolution may be required to discriminate between at least two positions along the line of response 206 joining two such detectors. The photons are emitted in opposite directions along the line of response 206 and are detected by detectors placed on the line of response 206.

PET data may be acquired in either a two-dimensional (2D) or three-dimensional (3D) mode. In the 2D acquisition mode, lines of responses 206 occurring in the same ring 218 or immediately adjacent ring 218 are accepted. In the 3D mode, any line of response 206 occurring between any pair of detector rings 218 is acquired. In the 2D mode, the annihilation events 204 that are acquired within the same detector ring 218 contribute to the direct planes, while those events 204 across neighboring rings 218 contribute to the cross planes.

Figure 3:
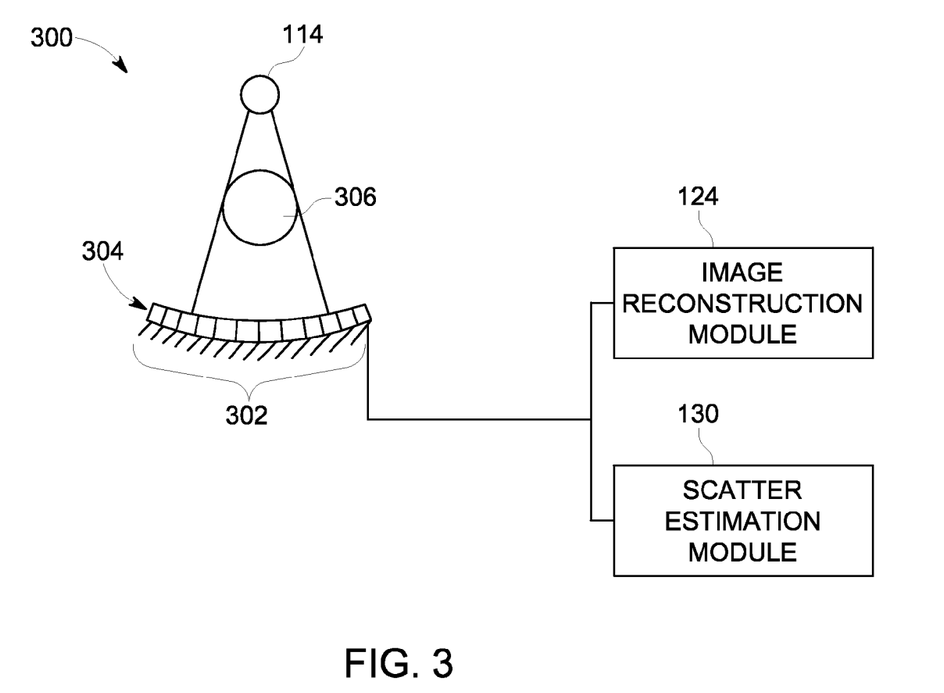
FIG. 3 is a diagram of a CT detector that acquires CT data for constructing a CT sinogram used in various embodiments.

It should be noted that CT data may be similarly binned based on different image views or projections views acquired across the CT detector, such as acquiring sinogram data using a transmission CT scan. For example, a CT imaging portion 300 may be provided as shown in FIG. 3 that includes an x-ray source, for example, the x-ray tube 114 and a detector 302. The detector 302 includes a plurality of detector elements 304 that are arranged in rows and channels, that together sense projected x-rays, from the x-ray tube 114 that pass through an object, such as a patient 306. Each detector element 304 produces an electrical signal, or output, that represents the intensity of an impinging x-ray beam and hence allows estimation of the attenuation of the beam as the beam passes through the patient 306. The projection data received from the detectors 304 is processed by the image reconstruction processor 124 to reconstruct an image of the object, for example, the patient 306. The scatter estimation module 130 is also programmed to reduce and/or eliminate scatter errors in the reconstructed image.

Figure 4:
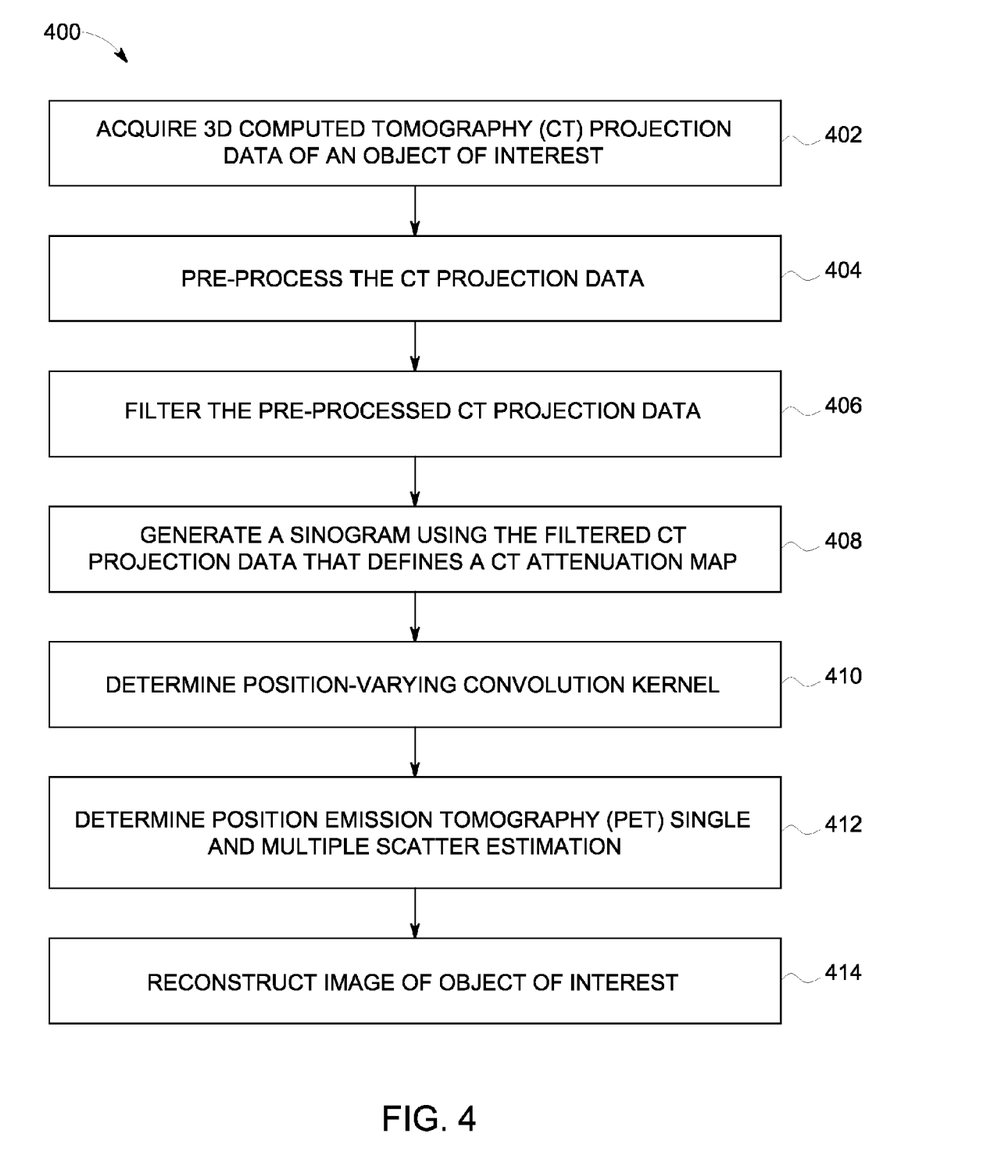
FIG. 4 is a flowchart of a method for estimating scatter in PET for image reconstruction in accordance with various embodiments.

In various embodiments, a method 400 as illustrated in FIG. 4 is provided for estimating scatter in 3D PET, which includes multiple scatter estimation, which may be used in reconstructing an image. The method 400 may be embodied as a set of instructions that are stored on a computer and implemented using, for example, the scatter estimation module 130. In particular, at 402, CT projection data is acquired. For example, a plurality of image views using the imaging system 100 (shown in FIG. 1) are acquired. Optionally, the CT projection data may be acquired from a memory device configured to store projection data from previous imaging scans.

At 404, the CT projection data may be preprocessed to generate preprocessed CT projection data. In one embodiment, preprocessing the CT projection data may include, for example, applying a detector gain-calibration, a reference channel normalization, and/or other suitable corrections to the CT projection data. Preprocessing the CT projection data may also include using various other techniques to preprocess the CT projection data.

It should be noted that electronic noise caused by the detector or a Data Acquisition System (DAS) coupled to the detector, may result in low signals. A low signal is generally a signal that includes a plurality of photon counts that is approximately equal to, or the same magnitude as the noise level of the DAS system. A negative signal is one example of a low signal. The negative signals are turned into positive values prior to a log operation being performed on the projection data to form a reconstructed image, because the log operation cannot accept negative values as input.

Accordingly, at 406 the pre-processed projection data is filtered, for example, to reduce the impact of the electronic noise that results in shading artifacts in a reconstructed image. The filtering may be performed using any suitable process, for example, such that detector samples having negative values are replaced with a positive value. The filtering may be an iterative process performed a number of times to reduce or remove shading from the pre-processed projection data.

As another example, adaptive filtering techniques may be used to reduce streak artifacts, such as using a smoothing operation. The smoothing operations generally involve adjusting the signal detected at one channel based on the detected signal magnitude at the channel and the magnitudes of the detected signals of adjacent channels. Such smoothing is performed on a channel by channel basis to eliminate streaking type artifacts.

Thereafter, at 408, after the preprocessed CT projection data has been filtered, the filtered projection data is used to generate a sinogram, which in one embodiment is a filtered attenuation sinogram. The filtered attenuation sinogram may be generated using any CT sinogram generation method and generally defines a CT attenuation map with respect to the imaged patient or object.

It should be noted that although the method 400 is described in connection with using CT projection data, the various embodiments may use data from other modalities to, for example, derive the attenuation map. For example, the various embodiments may use MR or atlas-based data and/or methods, such as to derive the attenuation map (e.g., attenuation sinogram). Thus, for example, in another embodiment, an MR-derived attenuation map is used instead of a CT-derived attenuation map.

Thereafter, a position-varying convolution kernel is determined at 410, which in one embodiment, includes using a kernel that varies in amplitude and width as a function of the filtered attenuation sinograms generated at 408.

In particular, a position-varying convolution kernel is calculated based on a plurality of parameters that, in one embodiment, are PET scanner specific. Accordingly, the determined parameters may be determined for a single PET scanner, a particular model of PET scanners (e.g., a particular PET scanner configuration), etc. For example, in some embodiments, five parameters are determined from computer simulation data, which may include Monte Carlo simulations used to generate data sets that includes both single and multiple scatter events. The data sets then may be used to optimize the parameters.

In one embodiment, the five optimized parameters used to calculate the position-varying kernel (as described in more detail below) are as follows: one parameter is used as the width of a Gaussian kernel to filter the path length sinogram and the other four parameters are the linear coefficients of the single to multiple, convolution kernel amplitude and width, which are assumed, in this embodiment, to be linearly related to the filtered path length. It should be noted that different numbers and types of parameters may be used as desired or needed.

Thereafter, at 412, PET single scatter estimation and PET multiple scatter estimation is determined. For example, single scatter estimation may be performed using any suitable single scatter estimation method, for example, as described in U.S. Pat. No. 7,312,455.

Additionally, using the position-varying convolution kernel and the predetermined parameters, PET multiple scatter estimation may be determined. More particularly, in various embodiments, the scattered PET data includes single, multiple scatters (including doubles, namely scattered twice), which may be defined as follows:

$$S_{total} = S_f + S_m \quad (1)$$

and the multiple scatter distribution can be estimated as an integral transformation of the single scatter distribution as follows:

$$S_m(r,\phi,z) = \iint S_f(r-u,\phi,z-\zeta)k(u,\zeta;\phi)dud\zeta \quad (2)$$

where $S_m(r,\phi,z)$ is the projection sinogram of multiple scatters, $S_f(r,\phi,z)$ is the sinogram of single scatters, and $\phi$ is the projection angle.

Because the single scatter model may be calculated using a few thick image slices, the convolution kernel can be simplified to a one-dimensional Gaussian (ignoring the variation along the z direction) as follows:

$$k(u;r,\varphi) = \frac{A(r,\varphi)}{\sigma(r,\varphi)} \cdot \exp\left(\frac{-u^2}{2\sigma(r,\varphi)}\right) \quad (3)$$

The amplitude (A) and kernel width ($\sigma$) are then assumed to be functions of the sinograms of path lengths $l(r,\phi)$, which can be calculated from the attenuation sinogram (map) of the object as follows:

$$l(r,\phi) = -\ln(att(r,\phi)) \quad (4)$$

where $att(u,\phi)$ is the attenuation map.

It should be noted that the kernel amplitude (A) and kernel width ($\sigma$) have approximately a linear relationship, for example, with respect to a cylindrical diameter object.

The kernel amplitude (A) and kernel width ($\sigma$) are also proportional to the mean path lengths as follows:

$$A = al + b \quad (5)$$

$$\sigma = cl + d \quad (6)$$

In various embodiments, a smoothed path length $l_f(r,\phi)$ (instead of a mean path length) with a Gaussian kernel $g(r,\sigma_l)$, is used to calculate the amplitude $A(r,\phi)$ and width $\sigma(r,\phi)$ of the convolution kernel (Equation 3 above) for objects with a distributed activity as follows:

$$l_f(r,\phi) = l(r,\phi) \otimes g(r,\sigma_l) \quad (7)$$

$$A(r,\phi) = a \cdot l_f(r,\phi) + b \quad (8)$$

$$\sigma(r,\phi) = c \cdot l_f(r,\phi) + d \quad (9)$$

where $l_f$ is the smoothed path length, $A(r,\phi)$ is the convolution amplitude and $\sigma(r,\phi)$ is the convolution width.

Figure 5:
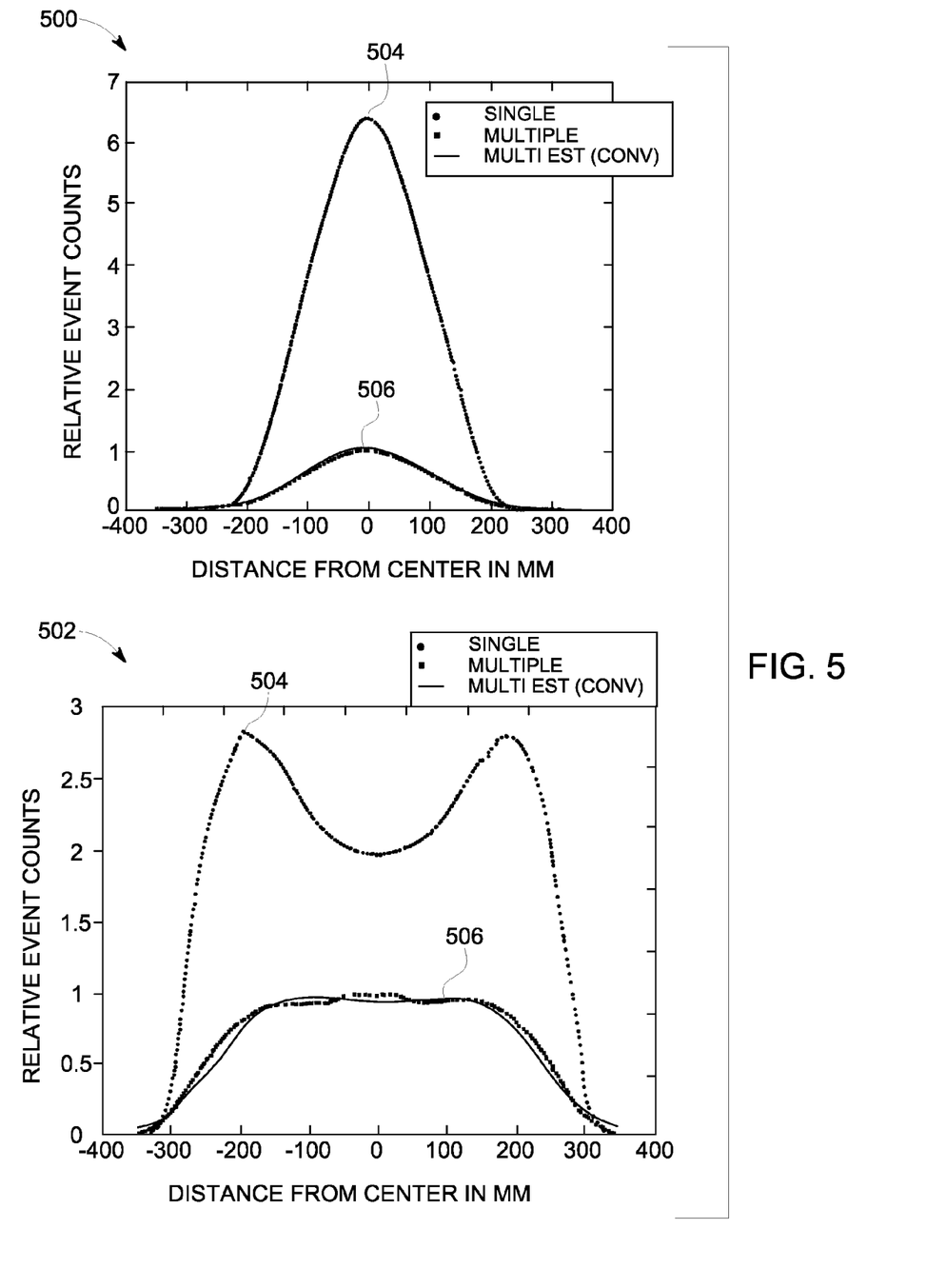
FIG. 5 are graphs illustrating a least squares fitting in accordance with various embodiments.

The five parameters, namely, a, b, c, d and $\sigma_l$ are determined in one embodiment, using a least squares fitting (from single scatter and multiple scatter), which is illustrated in the graphs 500 and 502 of FIG. 5. The graphs 500 and 502 illustrate fitting curves 504 and 506 for single and multiple scatters, respectively, that correspond to 20 cm and 45 cm flood simulation data used for parameter optimization.

Figure 6:
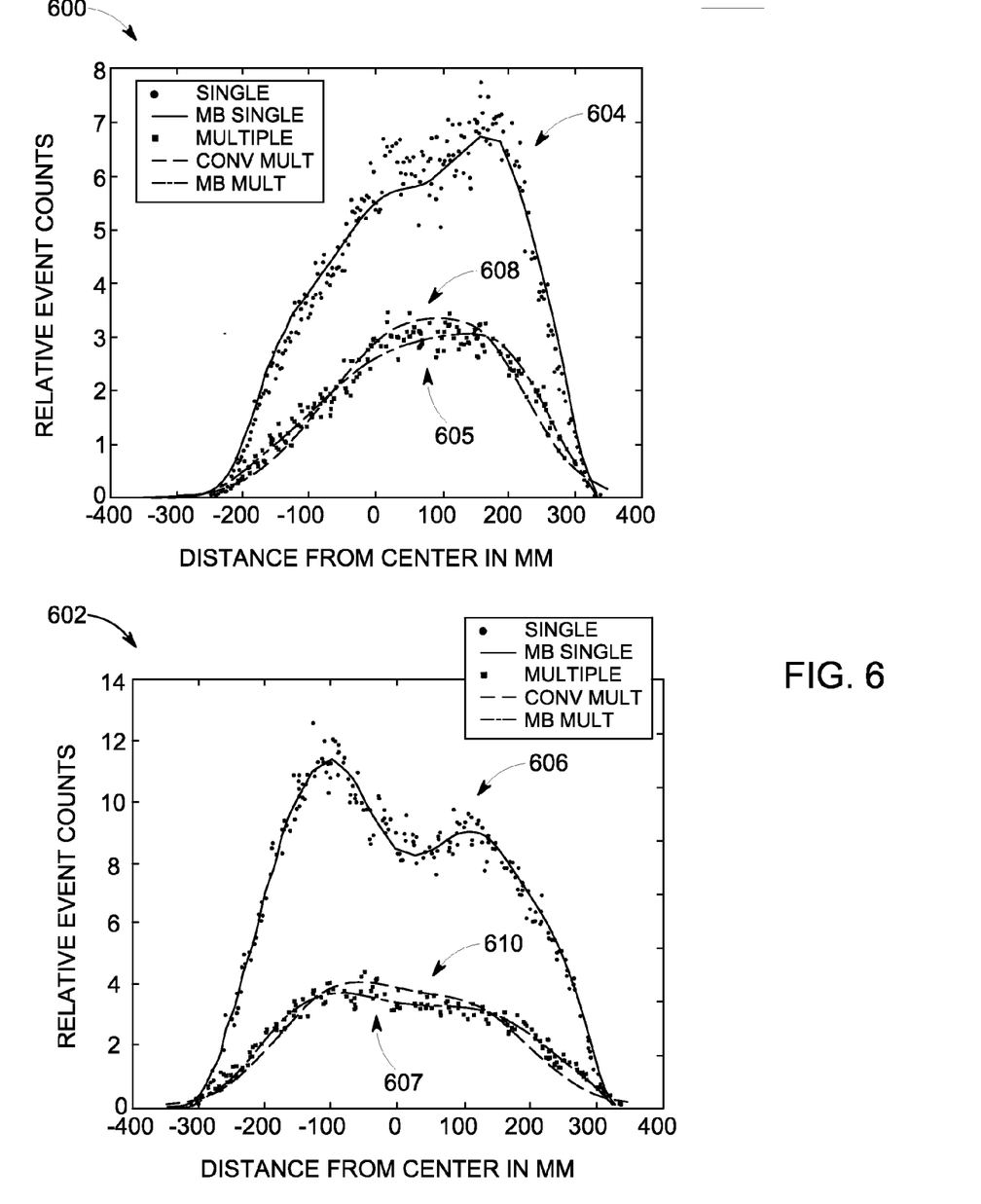
FIG. 6 are graphs illustrating sinogram profiles and results of model-based multiple scatter calculations in accordance with various embodiments.

Thus, various embodiments of a convolution method for multiple scatter estimation provide scatter estimation for different types and shapes of objects. For example, the graphs 600 and 602 of FIG. 6 show curves 604 and 606, which are Monte Carlo single scatter sinogram profiles. In FIG. 6, the curves 605 and 607 are Monte Carlo multiple scatter sinogram profiles and the curves 608 and curves 610 correspond to sinogram profiles resulting from multiple scatter estimation using the convolution methods of the various embodiments with position-varying kernels. As can be seen, the results represented by the curves 608 and 610 match well with the curves 605 and 607.

Figure 7:
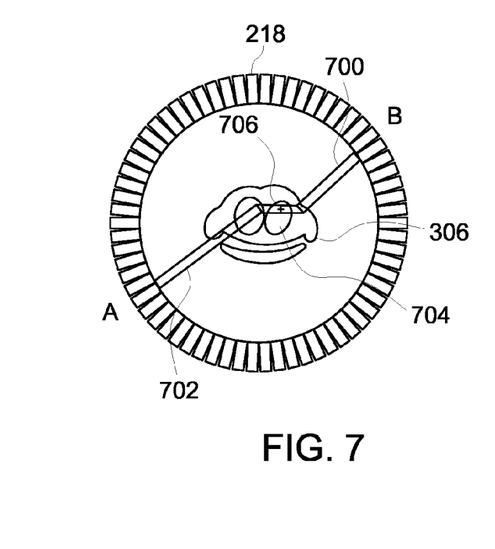
FIG. 7 is a diagram illustrating scatter that is corrected in accordance with various embodiments.

The various embodiments may be used, for example, for scatter correction during a cardiac PET exam. As shown in FIG. 7, multiple scatters illustrated by the scatter lines 700 and 702 may result from the emission of a radionuclide uptake and distribution into a heart 706 of the patient 306. These scatter events that cause the emissions to be detected by the ring 218 of detectors at two locations not along a straight line, may be corrected using the scatter estimation of the various embodiments.

Thus, a parameterized kernel amplitude (A) and width ($\sigma$) are used in combination with a CT attenuation map to estimate PET scatter, in particular, multiple scatters in 3D PET. The parameters are determined, for example, from simulations.

Referring again to the method 400 of FIG. 4, an image of the object of interest may then be reconstructed at 414, which is scatter corrected as described herein. The image reconstruction may be performed using any suitable PET reconstruction method.

Figure 8:
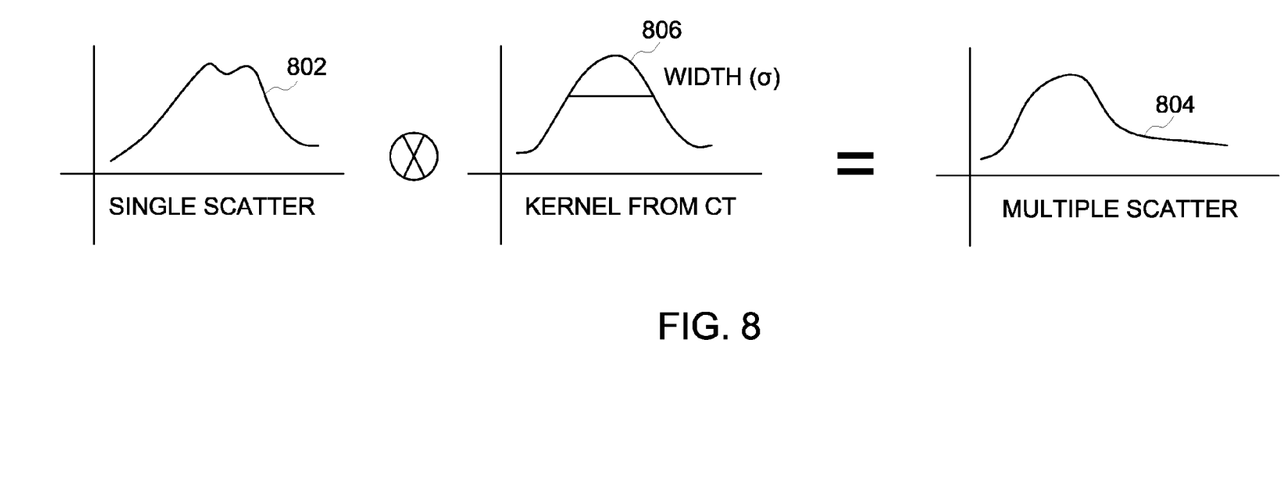
FIG. 8 is a diagram illustrating a determination of a kernel in accordance with various embodiments.

Thus, the kernel amplitude (A) and width ($\sigma$) are not constant, but object and view dependent based, for example, on a Gaussian distribution (and not an average of an attenuation map). Accordingly, as illustrated in FIG. 8, a curve 804 representing a multiple scatter distribution may be defined by the convolution of a curve 802 representing a single scatter distribution and a kernel from CT represented by the curve 806. In various embodiments, the single and multiple scatter distributions are known from simulation, for example, from simulations with a system model of a particular PET scanner. The kernel then may be determined and further optimized, such as, for different size objects, for example, larger and smaller patients. Thus, Gaussian shaped kernel varies at each detector position of the PET system. Accordingly, in various embodiments, the kernel varies over a radial length of the PET system.

It should be noted that variations and modifications are contemplated. For example, the various embodiments may be used in connection with Time-of-Flight (TOF) PET. In TOF PET, the various embodiments use a model in multiple time frames (e.g., five time frames) and then combine the models together (e.g., average the models). In operation, the model is then applied to each TOF frame separately to separate the activity distribution along the view line.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A non-transitory computer readable storage medium for estimating multiple scatter in Positron Emission Tomography (PET) imaging using a processor, the non-transitory computer readable storage medium including instructions to command the processor to:
   determine attenuation sinograms;
   determine a position-varying convolution kernel as a function of the attenuation sinograms, the kernel varying in amplitude and width over a radial length of a PET imaging system; and
   use the position-varying convolution kernel to estimate multiple PET scatter.

2. The non-transitory computer readable storage medium of claim 1, wherein the attenuation sinograms are determined from one of a Computed Tomography (CT) scan or a Magnetic Resonance (MR) scan and the instructions further command the processor to determine the position-varying convolution kernel with a Gaussian distribution of a CT attenuation map or an MR attenuation map using the attenuation sinograms.

3. The non-transitory computer readable storage medium of claim 1, wherein the instructions further command the processor to determine the position-varying convolution kernel using a single scatter distribution profile and a multiple scatter distribution profile, the single scatter distribution profile and the multiple scatter distribution profile determined from one or more simulations.

4. The non-transitory computer readable storage medium of claim 3, wherein the simulation is one of PET scanner specific or PET scanner configuration specific.

5. The non-transitory computer readable storage medium of claim 4, wherein a plurality of parameters used to determine the position-varying convolution kernel are determined from the one or more simulations, wherein one parameter defines a width of a Gaussian kernel to filter a path length sinogram and a plurality of additional parameters define linear coefficients of a single to multiple convolution kernel amplitude and width.

6. The non-transitory computer readable storage medium of claim 1, wherein the attenuation sinograms comprise filtered attenuation sinograms.

7. The non-transitory computer readable storage medium of claim 1, wherein the instructions further command the processor to use Time-of-Flight (TOF) information to determine the position-varying convolution kernel.

8. The non-transitory computer readable storage medium of claim 1, wherein the instructions command the processor to filter the amplitude and width with a determined path length.

9. A method for estimating multiple scatter in Positron Emission Tomography (PET) imaging, the method comprising:
determining attenuation sinograms;
determining a position-varying convolution kernel as a function of the attenuation sinograms, the kernel varying in amplitude and width over a radial length of a PET imaging system; and
using the position-varying convolution kernel to estimate multiple PET scatter.

10. The method of claim 9, wherein the attenuation sinograms are determined from one of a Computed Tomography (CT) scan or a Magnetic Resonance (MR) scan and further comprising determining the position-varying convolution kernel with a Gaussian distribution of a CT attenuation map or an MR attenuation map using the attenuation sinograms.

11. The method of claim 9, further comprising determining the position-varying convolution kernel using a single scatter distribution profile and a multiple scatter distribution profile, the single scatter distribution profile and the multiple scatter distribution profile determined from one or more simulations, wherein the simulation is one of PET scanner specific or PET scanner configuration specific.

12. The method of claim 11, wherein a plurality of parameters used to determine the position-varying convolution kernel are determined from the one or more simulations, wherein one parameter defines a width of a Gaussian kernel to filter a path length sinogram and a plurality of additional parameters define linear coefficients of a single to multiple convolution kernel amplitude and width.

13. The method of claim 9, further comprising using Time-of-Flight (TOF) information to determine the position-varying convolution kernel.

14. The method of claim 9, further comprising filtering the amplitude and width with a determined path length.

15. A Positron Emission Tomography (PET) imaging system comprising:
a gantry;
a detector ring mounted to the gantry, the detector ring having a plurality of detector elements; and
a scatter estimation module configured to (i) determine attenuation sinograms, (ii) determine a position-varying convolution kernel as a function of the attenuation sinograms, the kernel varying in amplitude and width over a radial length of the gantry, and (iii) use the position-varying convolution kernel to estimate multiple PET scatter.

16. The PET imaging system of claim 15, wherein the attenuation sinograms are determined from one of a Computed Tomography (CT) scan or a Magnetic Resonance (MR) scan and further comprising a CT imaging portion or an MR portion and wherein the scatter estimation module is further configured to determine the position-varying convolution kernel with a Gaussian distribution of a CT attenuation map or MR attenuation map using the attenuation sinograms determined from CT data or MR data acquired from the CT imaging portion or the MR imaging portion.

17. The PET imaging system of claim 15, wherein the scatter estimation module is further configured to determine the position-varying convolution kernel using a single scatter distribution profile and a multiple scatter distribution profile, the single scatter distribution profile and the multiple scatter distribution profile determined from one or more simulations, wherein the simulation is one of PET scanner specific or PET scanner configuration specific.

18. The PET imaging system of claim 17, wherein a plurality of parameters used to determine the position-varying convolution kernel are determined from the one or more simulations, wherein one parameter defines a width of a Gaussian kernel to filter a path length sinogram and a plurality of additional parameters define linear coefficients of a single to multiple convolution kernel amplitude and width.

19. The PET imaging system of claim 15, wherein the scatter estimation module is further configured to use Time-of-Flight (TOF) information to determine the position-varying convolution kernel.

20. The PET imaging system of claim 15, wherein the scatter estimation module is further configured to filter the amplitude and width with a determined path length.

* * * * *